United States Patent [19]

Tebbetts

[11] Patent Number: 5,498,257

[45] Date of Patent: Mar. 12, 1996

[54] CARTILAGE AND GRAFT PALETTE

[76] Inventor: John B. Tebbetts, 1928 W. Colorado, Dallas, Tex. 75208

[21] Appl. No.: 104,544

[22] Filed: Aug. 11, 1993

[51] Int. Cl.$^6$ ........................................ A61B 19/00
[52] U.S. Cl. ................................ 606/1; D24/227
[58] Field of Search .................... 600/36; 606/1; D24/224, 227; 206/564, 557, 370

[56] References Cited

U.S. PATENT DOCUMENTS

| | | | |
|---|---|---|---|
| 926,977 | 7/1909 | Brun | 206/564 |
| 3,851,808 | 12/1974 | Schilling | 206/557 |
| 4,889,231 | 12/1989 | Foote et al. | 206/363 |
| 4,991,718 | 2/1991 | Withers | 206/557 |
| 5,108,926 | 4/1992 | Klebe | 600/36 |
| 5,253,568 | 10/1993 | Prella et al. | 206/564 |
| 5,298,012 | 3/1994 | Handlos | 600/36 |

Primary Examiner—Stephen C. Pellegrino
Assistant Examiner—Glenn Dawson
Attorney, Agent, or Firm—Paul M. Craig, Jr.

[57] ABSTRACT

A cartilage and graft palette structure with a bottom, upwardly extending front and rear walls and two lateral walls interconnecting the front and rear walls to form the frame of a generally rectangular tray-like structure, as viewed in plan view. The front and rear walls as well as the lateral walls are of predetermined thickness to assure structural stability of the palette structure and to provide a peripheral rim having a sufficient width to accommodate at least a scale along the top of one of the walls. The bottom has an upper non-metallic surface which minimizes unsatisfactory tactile feedback to the surgeon by way of a surgical instrument and reduces the risk of slippage as a cartilage or graft is cut. The palette structure also offers sufficient fluid-tightness on the inside of the tray-like structure to enable maintenance of moisture of any graft or cartilage.

39 Claims, 1 Drawing Sheet

CARTILAGE AND GRAFT PALETTE

FIELD OF INVENTION

The present invention relates to a cartilage and graft palette and more particularly to a cartilage and graft palette which can be hand-held by the surgeon.

PRIOR ART

Surgical tray-like structures of the most varied types are known in the prior art. For example, U.S. Pat. No. 3,797,652 to Chesky discloses sterile shielded containers which can be stacked. U.S. Pat. No. 4,595,102 to Kerry et al. discloses a kit for performing medical procedures in which recesses are provided in a procedure tray to receive procedural components while a prepping tray is provided with recesses to receive prepping components. U.S. Pat. No. 4,844,249 to Coulombe discloses a medical supplies container consisting of a base wall, four upright side walls and a peripheral flange projecting outwardly from the top edge of the side walls and provided with bores engageable by hypodermic syringes and the like. A surgical procedure tray for supporting disposable medical devices is disclosed in U.S. Pat. No. 4,889,231 to Foote which consists of a flat bottom and a border surrounding the periphery of the bottom whereby the border has bends and an upwardly extending lip of predetermined thickness. Other tray-like structures are known in the art for transporting and/or storing surgical equipment. For example, U.S. Pat. No. 5,165,539 to Weber et al. discloses a surgical instrument transport tray consisting of a base and side walls terminating in outwardly extending lips which is adapted to be stored in a sterilization pan. The U.S. Pat. No. 5,195,538 to Eldridge et al. also discloses a surgical instrument tray, capable to cooperate with either a magnetic or non-magnetic surgical drape to retain medical instruments during surgery. Still other prior art patents relate to trays and arrangements for sterilizing surgical instruments. For example, U.S. Pat. No. 4,046,254 to Kramer relates to a surgical instrument tray which can be used for holding surgical instruments during sterilization and storing thereof. A more complex arrangement for sterilizing, transporting or storing for later use is shown in U.S. Pat. No. 5,098,676 to Brooks which consists of a box-like base of a mat that can be fitted into the base and of a cover which, when placed over the base, will not come in contact with any surgical instruments in the tray. A still more complex surgical tray system is disclosed in U.S. Pat. No. 5,174,453 to Stoeffler which includes a base, a U-shaped rack and an assembly tray as well as a cover. A container serving as a sterilization chest for surgical instruments is disclosed in U.S. Pat. No. 4,402,407 to Maly in which a box-like structure made from injection-molded plastics is reinforced in the bottom and sides thereof, and the upper edge of the box-like structure is provided with a peripheral flange. Various designs for surgical instrument trays are shown in U.S. Design Pat. Nos. 248,871 and 249,362 to Forsman et al. as well as in U.S. Design Pat. No. 276,462 to Villarreal and U.S. Design Pat. No. 282,279 to Holewinski et al. Moreover, instrument trays of special design are exemplified by U.S. Pat. No. 4,577,755 to Ramsay, U.S. Pat. No. 5,005,590 to Eldridge et al. and U.S. Pat. No. 5,097,963 to Chernosky et al. Commercially available have been devices in the form of small flat plates with grid markings at 1 mm. intervals made from stainless steel or of glass. These as also any similar devices were used to place a cartilage onto the device in order to determine its dimensions. However, they were never specifically recommended as a carving block on which the cartilage could be fabricated. The markings provided on these prior art devices allowed grafts, once tailored at another location or on this device, to be measured prior to reimplantation.

None of these prior art devices were specifically designed for graft fabrication with the ability to simultaneously retain moisture on the grafts. Any liquid placed on the flat stainless steel or glass plates could easily flow off, thereby preventing maintenance of moisture of the grafts. Moreover, the grafts themselves can easily slip off such flat, plate-like devices and possibly even fall off the sterile field because there is no lip on such flat plate-like devices. Additionally, metal or glass surfaces are unsatisfactory for actually fabricating grafts because the metal-to-metal contact of the scalpel blade with the glass or metal surface causes distasteful tactile feedback through the instrument, not to mention the fact that both the blade and graft can easily slip on these surfaces. Similarly, none of the prior art surgical tray structures as disclosed in the aforementioned prior art patents were designed as cartilage and graft palette nor would they be useful for the intended purposes of this invention for one or more reasons pointed out with the flat plate-like devices.

SUMMARY OF THE INVENTION

It is a principal object of the present invention to provide a cartilage and graft palette which avoids the shortcomings and drawbacks encountered with the prior art devices and which additionally can be hand-held by the surgeon during surgical operations. The underlying problems are solved according to the present invention by a cartilage and graft palette forming a tray-like structure of generally rectangular shape made from metal such as stainless steel in which the bottom is integrally formed with upwardly extending side walls forming a rim of sufficient width to accommodate markings for length determinations as well as other information such as name of the instrument. At least the upper surface of the bottom is made from a material other than metal or glass to avoid tactile feedback through the instrument and minimize slippage. In one preferred embodiment, the bottom consists of two parts, whereby the lower bottom part which is integral with the side walls is made from a metallic material while the upper bottom part which is constructed as a pad-like member and adapted to be inserted and removed, is made of a material such as urethane or Delrin. In that case, the bottom part and integrally formed side walls can be made of stainless steel which is preferred by some doctors for ease of sterilization. However, it is also possible to make the entire cartilage and graft palette of a plastic material such as urethane or Delrin, in which case the two-partite bottom becomes unnecessary. The dimensions as well as the outer contour of the cartilage and graft palette in accordance with the present invention are thereby such that the palette can be held by hand during surgical operations without discomfort to the surgeon. The palette of this invention is of sufficient overall dimensions on the inside of the tray-like structure including its depth that all expected surgical steps can be readily performed and unacceptable fluid loss is avoided.

There are several distinct advantages attainable by the cartilage and graft palette in accordance with the present invention. It provides an instrument that allows harvested cartilages to be stored without risk of slipping from the instrument. It assures maintenance of moisture of the grafts, if desired, by placing either a saline liquid or other suitable liquid in the tray with the cartilage grafts. It additionally provides a surface on which the grafts can be fabricated without having to remove them from the palette to another location for the fabrication. Last, but not least, it assures a surface that provides optimal accuracy and comfort as the grafts are cut.

BRIEF DESCRIPTION OF THE DRAWINGS

These and other objects, features and advantages of the present invention will become more apparent from the following description when taken in connection with the accompanying drawing which shows, for purposes of illustration only, one embodiment in accordance with the present invention, and wherein.

DETAILED DESCRIPTION OF THE DRAWINGS

Figure 1:
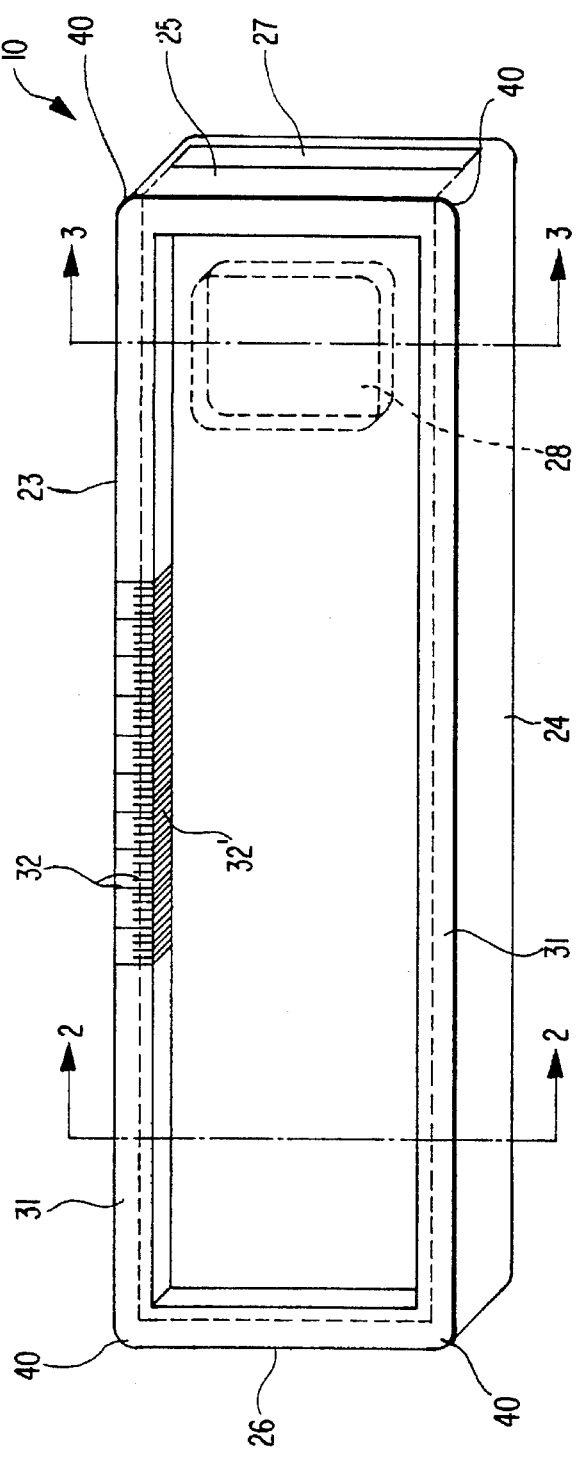
FIG. 1 is a perspective view from above and the side on a cartilage and graft palette in accordance with the present invention.
Figure 3:
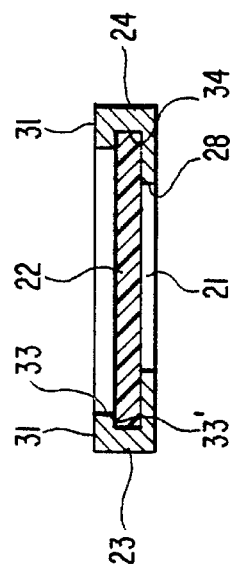
FIG. 3 is a cross-sectional view, taken along line III—III of FIG. 1.
Figure 2:
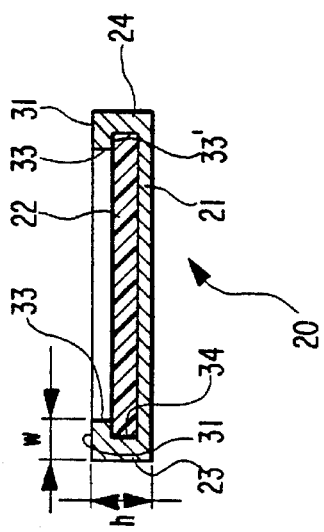
FIG. 2 is a cross-sectional view, taken along line II—II of FIG. 1.

Referring now to the drawing wherein like reference numerals are used throughout the various views to designate corresponding parts, the cartilage and graft palette in accordance with the present invention, generally designated by reference numeral 10 includes a base generally designated by reference numeral 20 (FIG. 2) which consists of a lower bottom part 21 and of an upper pad-like bottom part 22. The lower bottom part 21 is thereby made integrally with the upwardly extending longitudinal walls 23 and 24 and with the upwardly extending end walls 25 and 26. The upper pad-like bottom member 22 is made separate from the bottom part 21 and can be inserted and removed from the tray-like palette structure. For that purpose, a slot 27 is provided in the front wall 25 which is of such dimension that the upper wall part 22 can be inserted and removed therethrough. To facilitate insertion and removal of the upper bottom part 22, the lower bottom part 21 is provided with an opening 28 within the area near the end wall containing the slot in the illustrated embodiment in the area near the front wall 25. As can be seen from FIG. 1, the walls 23, 24, 25 and 26 are of such thickness that a shelf-like rim 31 is formed which extends peripherally about the tray-like palette structure. The width of this peripheral shelf-like rim 31 is such that it will accommodate a scale 32 of appropriate length in suitable increments to permit measurements during surgery of any removed graft or cartilage. This scale 32 is preferably carried down along the inside of the corresponding side wall as indicated at 32' in FIG. 1. In order to assure secure seating of the pad-like bottom member 22 and provide sufficient fluid-tightness of the tray-like structure, the walls 23, 24, 25 and 26 are provided with undercuts 34 to form inwardly extending lips 33 so that the removable bottom part 22 is securely held in place between the lower surfaces 33' of these lips and the top surface of the lower wall part 21, whereby the pressure exerted on the pad-like member of the bottom part 22 by proper selection of the dimensions produces the requisite fluid-tightness.

The dimensions in the cartilage and graft palette structure of this invention also play an important role to achieve the advantages attainable thereby. More specifically, the total height h of the palette structure in accordance with the present invention is about 8 to about 9 mm. to accommodate other dimensions and provide some flexibility to assure that after the pad-like bottom member 22 is inserted into the base of the device, there remains a height for the lips 33 of at least about 3 mm. along the entire periphery of the tray-like structure for the secure retention of any cartilage and of any fluid in the tray-like structure. This approximately 3 mm. height of the lips 33 together with an approximately 3 mm. thickness of the inserted pad-like upper bottom part 22 plus a thickness of the lower wall part 21 of about 2 mm. totals 8 mm. This 8 to 9 mm. range simply allows another millimeter if desired to have more thickness beneath the pad-like upper bottom member 22 for additional stability. The width w of the shelf-like rim portion of about 5 mm. is necessary for structural stability as well as adequate width to print or otherwise affix the scale 32 which is preferably a 5 cm. scale in 1 mm. increments as well as the name of the device and/or any other information. Measurements can then be carried out to facilitate fabrication of the grafts. A wider shelf would make the instrument too wide for comfortable fit in the hand of the surgeon; or, if the total palette width is held constant, a wider shelf would unnecessarily limit the useful work space on the palette. Though there is no criticality for the 3 mm. thickness of the pad-like upper bottom part 22, the 3 mm. thickness provides adequate rigidity and decreases the risks of warping which would make it more difficult to insert or remove the bottom part 22 and/or might provide an uneven work surface. The purpose of this pad-like upper bottom part 22 made of an appropriate plastic material such as urethane or Delrin or of other polycarbonate materials, such as LEXAN is to allow the scalpel blade to contact a surface which does not provide unsatisfactory tactile feedback to the surgeon and does not tend to slip as the cartilage is being cut.

Moisture retention is assured in the illustrated embodiment by the pressure exerted by the lips 33 which extend inwardly along the periphery of the tray-like structure, on the pad-like wall member 22 which at the same time assures a firm seating thereof within the palette structure.

Preferred inside dimensions of the tray-like compartment and of the surface of the pad-like bottom member 22 are 35 mm. by 140 mm., based on two considerations. The pad-like bottom member 22 needs to be large enough to accommodate the maximal size of any cartilage usually harvested, for example, from the nose. The selected dimensions also reflect a compromise between maximizing the size of the work surface while maintaining an overall size of the instrument which can be comfortably held in the surgeon's hand without undue discomfort. Furthermore, the pad-like bottom member 22 should also provide a large enough surface to allow forceps and scalpels to be used with the pad-like surface area without restriction.

The 2 mm. internal undercut 34 (FIG. 2) underneath the 5 mm. wide shelf-like rim 31 in each side of the palette structure retains the pad-like bottom member 22 securely in the base of the instrument by the resulting 2 mm. overlap of the metallic frame over the surface of the pad-like member. The 5 cm. scale in 1 mm. increments is to permit measurements during surgery of any removed graft or cartilage. The slot 27 in the end face 25 allows the pad-like bottom member 22 to be inserted into the frame and to be removed therefrom. To facilitate insertion and particularly removal, an opening 28 of about 20 mm. by about 25 mm. is provided in the lower bottom part 21 of the frame. Insertion and removal of the pad-like member 22 is desirable because it allows the pad-like member 22 to be disposable and replaceable so as to provide an optimal unmarked surface for graft trimming and fabrication.

The rounded-off corners 40 of the instrument, which are formed by an external radius of curvature of about 5 mm.

and an internal radius of curvature of about 1.9 mm., have been specifically designed for surgeon comfort when the instrument is hand-held. Using devices which include square corners would cause significant discomfort to the surgeon's hand over any extended period of time when pressure is applied to hold the device firmly in the hand to prevent slippage. Such discomfort may cause the surgeon to grip the instrument less firmly, increasing the risk that the instrument and/or the cartilage will fall out of the sterile field of the palette structure.

In a preferred embodiment of the present invention, the frame formed by the lower bottom part 21 and the upwardly extending walls 23, 24, 25 and 26 are made of metal, such as 304 stainless steel, while the disposable pad-like bottom member 22 is made of a suitable plastic material having the requisite characteristics as regards hardness, etc., found, for instance, in polycarbonates. Urethane or Delrin are particularly suitable for the present invention.

Advantages mentioned above are attainable by the cartilage and graft palette in accordance with this invention, inter alia, by the particular dimensions which allow the palette to be held in the hand of the surgeon or placed on a table as the grafts are fabricated. The inclusion of a lip is also important to retain both the grafts and liquid as the grafts are fabricated. With the metal version for the frame structure 21, 23, 24, 25 and 26, the pad-like wall member 22 provides a more satisfactory cutting surface where the graft can be held stationary and the blade tends not to slide as the graft is being tailored. Moreover, there is no unsatisfactory tactile feedback.

However, a totally disposable version of the cartilage and graft palette in accordance with the present invention is also possible. In that case the same advantages are then attainable with a disposable version according to the present invention which is fabricated in one piece from a suitable plastic material such as urethane, Delrin or any other appropriate known material.

Furthermore, the advantages of the present invention are also attainable with a modified version of the cartilage and graft palette structure in which the pad-like bottom member, instead of being insertable by sliding it through a slot in an end wall, is adapted to be installed by being pressed into the tray-like structure of the palette from above. The pad-like member in this case will have a length and width as well as rounded-off corners, which correspond to the inside dimensions of the tray-like structure. With a length and width of the inside area of the palette structure, as viewed in plan view, of 140 mm. and 35 mm., the length and width of the pad-like member are 140 mm. max. and 35 mm. max., respectively. To facilitate installation and removal as well as secure seating, the pad-like bottom member may then also be provided with small elastic projections extending outwardly in the plane of the pad-like member along all sides thereof which are formed integrally with the pad-like bottom member during manufacture thereof by the use of known techniques. Furthermore, to facilitate removal of the pad-like bottom member, the latter may be provided with an opening of about 15 mm. in the longitudinal direction of the palette structure and about 20 mm. in the transverse direction of the palette structure and spaced about 7.5 mm. from the adjacent transverse end and about 7.5 mm. from adjacent longitudinal ends. As the pad-like member is pressed into the tray-like compartment of the palette from above, the need for any undercuts is obviated. Furthermore, fluid-tightness can be assured by eliminating the through-opening 28 of the embodiment of FIG. 1. However, to facilitate removal of the pad-like bottom member, an opening of about 20 mm. by about 25 mm. may be provided in the lower bottom part which is located so as to overlap with the through opening in the pad-like bottom member. However, the opening in the lower bottom member now extends no longer through the lower bottom part but only to a depth of about half the thickness of the lower bottom part, i.e., to a depth of about 2 mm. with a thickness of the lower bottom part of about 4 mm. Such opening may be provided also at both ends of the lower bottom part spaced about 5 mm. from the respective end of the internal dimensions of the tray-like structure. Of course, the corners of the pad-like member forming the upper bottom part are rounded-off in conformity with the rounding-off of the inner surface of the tray-like compartment of the palette structure. The pad-like bottom member may again consist of Delrin or urethane or some other suitable polycarbonate.

The cartilage and graft palette in accordance with the present invention may be manufactured by the use of conventional techniques as known to those skilled in the art.

While I have shown and described only one embodiment in accordance with the present invention, it is understood that the same is not limited thereto but is susceptible of numerous changes and modifications as known to those skilled in the art. In lieu of urethane or Delrin, also any other material having similar properties suitable for the purposes of the present invention can be used. Thus, the present invention is susceptible of numerous changes and modifications, and I therefore do not wish to be limited to the details shown and described herein but intend to cover all such changes and modifications as are encompassed by the scope of the appended claims.

I claim:

1. A cartilage and graft palette structure of a size to fit within a hand of a surgeon during surgical procedures, comprising bottom means extending over the full width and length of the palette structure, upwardly extending front, rear and lateral walls interconnecting said front and rear walls to form together with said bottom means a generally rectangular tray-like structure, as viewed in plan view on said palette structure, said bottom means, said front and rear walls as well as said lateral walls forming a frame for the palette structure, said walls being of such thickness as to assure structural stability of the palette structure and provide by such thickness a shelf-like peripheral rim having a sufficient width, as viewed in plan view on the palette structure, to accommodate indicia along the shelf-like rim of at least one of said walls, the bottom means having an upper non-metallic surface which minimizes unsatisfactory tactile feedback to the surgeon by way of a surgical instrument and reduces the risk of slippage as cartilage or graft is cut, and further means to assure sufficient fluid-tightness on the inside of the tray-like structure to enable maintenance of moisture of any graft or cartilage.

2. A cartilage and graft palette structure according to claim 1, wherein said bottom means is of two partite structure, one part of said bottom means having upper and lower surfaces and being integral with said walls to constitute a base for the frame of the tray-like structure, and the other part of said bottom means being insertable over and removable from said one bottom part and having said upper non-metallic surface.

3. A cartilage and graft palette structure according to claim 2, wherein said other bottom part is a pad-like base member adapted to be inserted and removed through a slot in one of the front and rear walls.

4. A cartilage and graft palette structure according to claim 3, wherein said slot has a height and width substantially corresponding to the thickness and width of the other bottom part.

5. A cartilage and graft palette structure according to claim 4, wherein said other bottom part has a thickness of about 3 mm., a width of about 39 mm. and a length of about 145 mm.

6. A cartilage and graft palette structure according to claim 3, wherein said one bottom part is provided with an opening within the area near said slot to facilitate insertion and removal of the other bottom part.

7. A cartilage and graft palette structure according to claim 2, wherein said further means includes lip means formed by undercuts along inner surfaces of said walls and of such height that the other bottom part is securely held in position between the undersurfaces of said lip means and the upper surface of said one bottom part.

8. A cartilage and graft palette structure according to claim 7, wherein the spacing between the undersurface of said lip means and the upper surface of said one bottom part is so selected that a desired fluid-tightness is achieved.

9. A cartilage and graft palette structure according to claim 8, wherein the height dimension of the undercuts in said walls is substantially equal to the thickness of said other bottom part.

10. A cartilage and graft palette structure according to claim 8, wherein the said other bottom part is made from a plastic material, and wherein said one bottom part and said walls are made from a metallic material.

11. A cartilage and graft palette structure according to claim 10, wherein said metallic material is stainless steel and said plastic material is urethane or Delrin.

12. A cartilage and graft palette structure according to claim 2, wherein said walls and said one bottom part form the frame for a one-piece metallic compartment in said tray-like structure, and wherein said other bottom part is made from a plastic material.

13. A cartilage and graft palette structure according to claim 12, wherein said plastic material is urethane or Delrin.

14. A cartilage and graft palette structure according to claim 2, wherein said other bottom part has width and length dimensions corresponding substantially to the internal width and length dimensions of said tray-like structure and is insertable into the tray-like structure from above.

15. A cartilage and graft palette structure according to claim 14, further comprising means to facilitate removal of said other bottom part from said tray-like structure.

16. A cartilage and graft palette structure according to claim 15, wherein said last-mentioned means includes small elastic projections integral with the other bottom part and extending outwardly from at least some of its sides.

17. A cartilage and graft palette structure according to claim 2, wherein said one bottom part has a thickness of about 2 mm. to about 3 mm. and said other bottom part has a thickness of about 3 mm.

18. A cartilage and graft palette structure according to claim 17, wherein an inside height of said walls from the top surface of the bottom means is about 3 mm.

19. A cartilage and graft palette structure according to claim 18, wherein said further means includes lip means which overlap the top surface of said bottom means by about 2 mm.

20. A cartilage and graft palette structure according to claim 1, wherein said non-metallic material is a polycarbonate, Delrin or urethane.

21. A cartilage and graft palette structure according to claim 1, wherein said walls and bottom means are one piece and made from a plastic material.

22. A cartilage and graft palette structure according to claim 21, wherein said plastic material is urethane or Delrin.

23. A cartilage and graft palette structure according to claim 21, wherein the thickness of said walls is of the order of 5 mm.

24. A cartilage and graft palette structure according to claim 1, wherein the inside dimensions of the tray-like structure are about 35 mm. by about 140 mm.

25. A cartilage and graft palette structure according to claim 24, wherein said other bottom part has a width of about 35 mm. and a length of about 140 mm.

26. A cartilage and graft palette structure according to claim 24, wherein said other bottom part has a thickness of about 3 mm., a width of about 39 mm. and a length of about 145 mm.

27. A cartilage and graft palette structure according to claim 1, wherein the thickness of said walls is of the order of 5 mm.

28. A cartilage and graft palette structure according to claim 27, wherein inside dimensions of the tray-like structure are about 35 mm. by about 140 mm.

29. A cartilage and graft palette structure according to claim 1, wherein corners of said generally rectangular tray-like structure are rounded-off.

30. A cartilage and graft palette structure according to claim 1, wherein indicia are provided on said peripheral rim which include a scale in 1 mm. increments with the scale and increments also carried down on an inside of said one wall.

31. A cartilage and graft palette structure which can be hand-held by a surgeon during surgical procedures, comprising bottom means, upwardly extending front, rear and two lateral walls forming together with said bottom means a generally rectangular tray-like structure, as viewed in plan view on the palette structure, said bottom mean, said front and rear walls as well as said lateral walls being of such thickness as to assure structural stability of the palette structure and provide by such thickness a shelf-like peripheral rim having a sufficient width, as viewed in plan view on the palette structure, to accommodate indicia along the shelf-like rim of at least one of said walls, the bottom means having an upper non-metallic surface which minimizes unsatisfactory tactile feedback to the surgeon by way of a surgical instrument and reduces the risk of slippage as cartilage or graft is cut, and inside dimensions of said tray-like structure being about 35 mm. by about 140 mm. with a thickness of said walls of about 5 mm. to permit said cartilage and graft palette structure to be hand-held by the surgeon during surgical procedures.

32. A cartilage and graft palette structure according to claim 31, wherein said bottom means is of two partite structure, one part of said bottom means being integral with said walls to constitute the base for the frame of the tray-like structure, and the other part of said bottom means being insertable over and removable from said one bottom part and having said upper non-metallic surface.

33. A cartilage and graft palette structure according to claim 31, wherein indicia are provided on said peripheral rim which include a scale in 1 mm. increments with the scale and increments also carried down on an inside of said one wall.

34. A cartilage and graft palette structure according to claim 31, wherein an inside height of said walls from the top thereof to the upper surface of the bottom means is about 3 mm.

35. A cartilage and graft palette structure, comprising means forming a one-piece frame of the palette structure including upwardly extending wall means defining an interior space of the palette structure and at least a bottom means extending over the full width and length of said palette structure, said wall means extending at substantially right angle to said bottom means and being of such thickness as to assure structural stability of the palette structure and provide by such thickness a shelf-like peripheral rim at the top end of said wall means, further bottom means adapted to be inserted into the palette structure over the first-mentioned bottom means, and further means to assure a desired fluid-tightness on the inside of the tray-like structure to enable maintenance of moisture of any graft or cartilage including undercuts along the inside of the wall means spaced a predetermined distance from the top thereof to form lip means extending inwardly, said undercuts being of such a dimension in the direction of the upwardly extending wall means that the pressure exerted by the underside of the lip means on the further bottom means produces the desired fluid tightness.

36. A cartilage and graft palette structure according to claim 35, wherein said dimension corresponds at least approximately to the thickness of said further bottom means.

37. A cartilage and graft palette structure according to claim 35, wherein said dimension corresponds, at most, to the thickness of said further bottom means.

38. A cartilage and graft palette structure according to claim 35, wherein the area of said further bottom means is larger than the area of the interior space by an amount not exceeding the depths of the undercuts.

39. A cartilage and graft palette structure according to claim 35, wherein said further bottom means has an upper surface minimizing tactile feedback to the surgeon by way of a surgical instrument.

* * * * *